(12) United States Patent
Yu et al.

(10) Patent No.: US 6,436,687 B1
(45) Date of Patent: Aug. 20, 2002

(54) CDNA SEQUENCE OF MOUSE BRAIN SIALIDASE GENE

(75) Inventors: Robert K. Yu; Chris Fronda; Guichao Zeng, all of Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/556,870

(22) Filed: Apr. 21, 2000

(Under 37 CFR 1.47)

Related U.S. Application Data

(60) Provisional application No. 60/130,712, filed on Apr. 22, 1999.

(51) Int. Cl.⁷ .............................. C12N 9/24; C12N 5/10; C12N 15/63; C12Q 1/34; C12P 21/06
(52) U.S. Cl. .................. 435/200; 435/18; 435/69.1; 435/325; 435/252.3; 435/320.1; 536/23.2
(58) Field of Search .......................... 435/200, 18, 325, 435/252.3, 320.1, 69.1; 536/23.2

(56) References Cited

PUBLICATIONS

Miyagi et al., J. Biol. Chem. 268:26435–26440, 1993 (Gen-EMBL accession number RATSILD).*

* cited by examiner

*Primary Examiner*—Ponnathapu Achutamurthy
*Assistant Examiner*—Delia M. Ramirez
(74) *Attorney, Agent, or Firm*—Whitham, Curtis & Christofferson, P.C.

(57) ABSTRACT

The present invention concerns mouse brain sialidase gene activity. The invention further relates to nucleic acids encoding sialidase protein, vectors containing and capable of expressing such nucleic acid, and recombinant host cells transformed with such nucleic acid. The invention also provides an amino acid sequence encoding an enzymatically active sialidase that is active in eukaryotic cells. The invention also provides host cells transfected or transformed with recombinant vectors expressing the sialidase gene from mouse brain in the host cells.

11 Claims, 1 Drawing Sheet

SEQUENCE LISTING

<160> NUMBER OF SEQ ID NOS: 6

<210> SEQ ID NO 1
<211> LENGTH: 1697
<212> TYPE: DNA
<213> ORGANISM: Mus musculus

<400> SEQUENCE: 1

```
ctcatggagc ttgcccccaa aaattgagag tgcacaaaag aaagaaataa gaaatagccc      60
agcccctact ttctggctgt gccagctgtc agaggcacag aaaaggtgtt gggggggcac     120
ccactgaagt ctccagattc tcctgtctca ggacaaggga cagcaccaag gacacatgga     180
agatctcagg cccatggcga cctgccctgt cctgcagaag gagacactgt tccgcacagg     240
cgtccatgct tacagaatcc ctgctctgct ctacctgaag aagcagaaga ccctgctggc     300
ctttgcggaa aggcgagcca gcaagacgga tgagcacgca gagttgattg tcctgagaag     360
aggaagctac aacgaagcca ccaaccgtgt caagtggcag cctgaggaag tggtgaccca     420
agcccagctg gaaggccacc gctccatgaa tccatgtccc ttgatgacaa gcaaaaaaga     480
cctcttcctt ttcttcatcg ctgtccctgg gcgtgtatca aacatcatc agctccacac      540
taaggttaat gtcacacggc tgtgctgtgt cagcagcact gaccatggga ggacctggag     600
ccccatccag gacctcacag agaccaccat tggcagcact catcaggaat gggccacatt     660
tgctgtgggt cctgggcatt gtctgcagct gcggaaccca gctgggagcc tgctggtacc     720
tgcttatgcc taccggaaac tgcaccctgc tcagaagcct accccctttg ccttctgctt     780
catcagcctt gaccatgggc acacatggaa actaggcaac tttgtggctg aaaactcact     840
ggagtgccag gtggctgagg ttggcactgg agctcagagg atggtatatc tcaatgctag     900
gagcttcctg ggaccagggt ccaggcaca aagtcctaat gatggtctgg atttccagga     960
caaccgggta gtgagtaagc ttgtagagcc ccccacggg tgtcatggaa gtgtggttgc     1020
cttccacaac cccatctcta agccacatgc cttagacaca tggcttcttt atacacaccc     1080
tacagactcc aggaatagaa ccaacctggg tgtgtaccta aaccagatgc cactagatcc     1140
cacagcctgg tcagagccca ccctgctggc catgggcatc tgtgcctact cagacttaca     1200
gaacatgggg caaggccctg aggctcccca cagtttgggt gtctgtatga atcaggtaac     1260
tatgaagaga tcattttcct catattcacc ctgaagcaag ctttccccac tgtatttgat     1320
gcccagtgat ctcagtgcac gtggcccaaa gggcttcctt gtgcttcaaa acacccatct     1380
ctctttgctt ccagcatcct ctggactctt gagtccagct cttgggtaac ttcctcagga     1440
ggatgcagag aatttggtct cttgactctc tgcaggcctt attgtttcag cctctggttc     1500
tcttttcagc ccagaaatca aaggagcctg gctttcctca gcctgttggc agggcaggtg     1560
gggacagtat atatagaggc tgccattctg catgtcggtt gtcactatgc tagtttaacc     1620
tgcctgtttc cccatgccta gtgtttgaat gagtattaat aaaatatcca acccagaaaa     1680
```
aaaaaaaaac aaaaaaa                                        1697

<210> SEQ ID NO 2
<211> LENGTH: 372
<212> TYPE: PRT
<213> ORGANISM: Mus musculus

<400> SEQUENCE: 2

```
Met Glu Asp Leu Arg Pro Met Ala Thr Cys Pro Val Leu Gln Lys Glu
 1               5                  10                  15

Thr Leu Phe Arg Thr Gly Val His Ala Tyr Arg Ile Pro Ala Leu Leu
            20                  25                  30

Tyr Leu Lys Lys Gln Lys Thr Leu Leu Ala Phe Ala Glu Arg Arg Ala
        35                  40                  45

Ser Lys Thr Asp Glu His Ala Glu Leu Ile Val Leu Arg Arg Gly Ser
 50                  55                  60

Tyr Asn Glu Ala Thr Asn Arg Val Lys Trp Gln Pro Glu Glu Val Val
 65                  70                  75                  80

Thr Gln Ala Gln Leu Glu Gly His Arg Ser Met Asn Pro Cys Pro Leu
            85                  90                  95

Met Thr Ser Lys Lys Asp Leu Phe Leu Phe Phe Ile Ala Val Pro Gly
            100                 105                 110

Arg Val Ser Glu His His Gln Leu His Thr Lys Val Asn Val Thr Arg
            115                 120                 125

Leu Cys Cys Val Ser Ser Thr Asp His Gly Arg Thr Trp Ser Pro Ile
        130                 135                 140

Gln Asp Leu Thr Glu Thr Thr Ile Gly Ser Thr His Gln Glu Trp Ala
145                 150                 155                 160

Thr Phe Ala Val Gly Pro Gly His Cys Leu Gln Leu Arg Asn Pro Ala
                165                 170                 175

Gly Ser Leu Leu Val Pro Ala Tyr Ala Tyr Arg Lys Leu His Pro Ala
            180                 185                 190

Gln Lys Pro Thr Pro Phe Ala Phe Cys Phe Ile Ser Leu Asp His Gly
        195                 200                 205

His Thr Trp Lys Leu Gly Asn Phe Val Ala Glu Asn Ser Leu Glu Cys
    210                 215                 220

Gln Val Ala Glu Val Gly Thr Gly Ala Gln Arg Met Val Tyr Leu Asn
225                 230                 235                 240

Ala Arg Ser Phe Leu Gly Ala Arg Val Gln Ala Gln Ser Pro Asn Asp
                245                 250                 255

Gly Leu Asp Phe Gln Asp Asn Arg Val Val Ser Lys Leu Val Glu Pro
            260                 265                 270

Pro His Gly Cys His Gly Ser Val Val Ala Phe His Asn Pro Ile Ser
        275                 280                 285

Lys Pro His Ala Leu Asp Thr Trp Leu Leu Tyr Thr His Pro Thr Asp
    290                 295                 300

Ser Arg Asn Arg Thr Asn Leu Gly Val Tyr Leu Asn Gln Met Pro Leu
305                 310                 315                 320

Asp Pro Thr Ala Trp Ser Glu Pro Thr Leu Leu Ala Met Gly Ile Cys
                325                 330                 335

Ala Tyr Ser Asp Leu Gln Asn Met Gly Gln Gly Pro Glu Ala Pro His
            340                 345                 350

Ser Leu Gly Val Cys Met Asn Gln Val Thr Met Lys Arg Ser Phe Ser
        355                 360                 365
```

```
Ser Tyr Ser Pro
    370

<210> SEQ ID NO 3
<211> LENGTH: 17
<212> TYPE: DNA
<213> ORGANISM: Artificial Sequence: Synthetic Primer
<220> FEATURE:
<221> NAME/KEY: misc_feature
<222> LOCATION: (1)..(17)
<223> OTHER INFORMATION: Artifical sequence: synthetic primer
      n connotes to a, t, g, or c.
<221> NAME/KEY: misc_feature
<222> LOCATION: (1)..(17)
<223> OTHER INFORMATION: Artifical sequence: synthetic primer

<400> SEQUENCE: 3
ctgctngcct ttgcnga                                              17

<210> SEQ ID NO 4
<211> LENGTH: 20
<212> TYPE: DNA
<213> ORGANISM: Artificial Sequence: Synthetic Primer
<220> FEATURE:
<221> NAME/KEY: misc_feature
<222> LOCATION: (1)..(20)
<223> OTHER INFORMATION: Artifical sequence: synthetic primer

<400> SEQUENCE: 4
tcrtacagrc acccaaaytg                                           20

<210> SEQ ID NO 5
<211> LENGTH: 27
<212> TYPE: DNA
<213> ORGANISM: Artificial Sequence: Synthetic Primer
<220> FEATURE:
<221> NAME/KEY: misc_feature
<222> LOCATION: (1)..(27)
<223> OTHER INFORMATION: Artifical sequence: synthetic primer

<400> SEQUENCE: 5
cctcttcctt ttcttcatcg ctgtccc                                   27

<210> SEQ ID NO 6
<211> LENGTH: 35
<212> TYPE: DNA
<213> ORGANISM: Artificial Sequence: Synthetic Primer
<220> FEATURE:
<221> NAME/KEY: misc_feature
<222> LOCATION: (1)..(35)
<223> OTHER INFORMATION: Artifical sequence: synthetic primer

<400> SEQUENCE: 6
tggtttaggt acacacaccc aggttggttc tattc                          35
```

CDNA SEQUENCE OF MOUSE BRAIN SIALIDASE GENE

This application claims benefit under 35 USC 119(e) of Provisional Application Ser. No. 60/130,712, filed Apr. 22, 1999, the entire contents of which is hereby incorporated by reference.

This invention was made using funds from grants from the National Institutes of Health having grant number NS-11853. The government may have certain rights in this invention.

BACKGROUND OF THE INVENTION

1. Field of the Invention

The present invention generally relates to a eukaryotic DNA sequence and, more particularly, to a eukaryotic cDNA sequence derived from mRNA encoding a sialidase enzyme, the MRNA being expressed in mouse brain cells.

2. Background Description

Sialidases are a family of glycohydrolytic enzymes which cleave sialic acid residues from the oligosaccharide components of glycoproteins and glycolipids. Sialidases have been identified in a number of cellular organelles: the plasma membrane, the lysosomes, and the cytosol (Schengrund, C., Rosenberg, A., and Repman, M. A. (1976) J. Biol. Chem., 79:555; Tulsiani, D.

R. P., and Carubelli, R., (1970) J. Biol. Chem., 245:1821). The sialidase enzyme has alternatively been referred to as "neuraminidase," and the names are considered synonymous within the relevant art. Saito, M. and Yu, R. K., "Biochemistry and Function of Sialidases" in *Biology of the Sialic Acids*, Plenum Press, N.Y. (1995).

In general, sialidase enzymes catalyze the release of sialic acid from sialo-oligosaccharides, gangliosides, or sialoglycoprotein. The sialic acid in the oligosaccharide component of glycoproteins is involved in mediation of clearance from the serum and thus affects the physical, chemical and immunogenic properties of the protein molecule. Maintenance of sialic acid residues is thus important to the functional expression of various glycoproteins with pharmaceutic uses as described in U.S. Pat. No. 5,928,915 to Warner et al. It is well known in the art that the oligosaccharide part of various glycoconjugates (especially glycolipids and glycoproteins) have a number of important functions in vivo (Biology of Carbohydrates, vol. 2, Ginsburg et al., Wiley, N.Y., 1984; The Glycoconjugates, vol. I–V, Academic Press, New York. Carbohydrate structures are important for the stability, activity, localization, immunogenicity and degradation of glycoproteins. Carbohydrates are antigenic determinants for blood group antigens and act as receptors for pathogens, proteins, hormones, and toxins, for example. Carbohydrates are also important for oncogenesis, since specific oligosaccharides have been found to be cancer-associated antigenic determinants. The cleavage of carbohydrate moieties from certain precursor glycoproteins, can result in the creation of potent immune stimulators. For example, group-specific component is a precursor of a macrophage activating factor that is normally converted to the active factor by the action of glycosidases of B and T cells. By way of example as an in vitro role for one particular sialidase, U.S. Pat. No. 5,177,002 to Yamamoto discloses a process for the production of a potent macrophage activating factor derived from human vitamin D-binding protein by cleaving Vitamin D protein with a combination of b-galactosidase and sialidase.

A number of bacterial and viral sialidase enzymes have been cloned, their X-ray crystal structures reported, and their biological functions extensively studied. It has been suggested that the *Vibrio cholerae* sialidase may function as a virulence factor for the bacterium, by increasing the binding affinity and penetration of cholera toxin into target cells. The sialidase of influenza virus has been suggested to play a role in the escape of progeny virus from infected cells. Thus, there are numerous sialidase enzymes in nature with a wide variety of physiological significance attributed to the different molecules.

Several mammalian forms of the gene encoding sialidase have been cloned, including rat muscle sialidase, Chinese hamster ovary (CHO) cell sialidase, and sialidases from mouse and human lysosomes. Rat skeletal sialidase has been purported to play a role in the differentiation of skeletal muscle cells. Desialyation of recombinant proteins expressed in CHO cells may result in a reduced clinical effect of such proteins. In addition, mouse and human lysosomal sialidases have been implicated in two metabolic storage disorders, namely sialidosis and galactosialidosis.

Sialidosis is a metabolic disorder that can be inherited as an autosomal recessive trait. It is caused by a deficiency of the enzyme alpha-neuramidinase, and it affects the metabolizing of certain fats and carbohydrates. In this condition an enzyme is missing that results in the accumulation of sialic acid in the nerve cells. The disorder is also associated with excess tissue accumulation and urinary excretion of sialylated oligosaccharides and glycolipids. There are two main clinical variants of the disease: late onset sialidosis type I, characterized by bilateral macular cherry-red spots and myoclonus, and infantile onset type II, which is characterized by skeletal dysplasia, mental retardation and hepatosplenomegaly. Galactosialidosis is distinguished from sialidosis by the additional deficiency in b-galactosidase enzyme activity and concurrent accumulation and excretion of excess sialyloligosaccharides.

Sialidase enzymatic activity has been reported previously in rat and mouse brains. In addition, a sialidase activity has been identified in brain myelin that may play a functional role in developmental changes in myelin gangliosides and membrane adhesion. Saito, M., and Yu, R. K.,*J. Neurochem.* 58, 83–37 (1992); Saito, M., and Yu, R. K., *J. Neurosci.* 36, 127–132 (1992). It has also been reported previously that two immunologically distinct forms of sialidase can be found in bovine brain, with one type localized to the synaptosomal membrane and one found in both synaptosomal and lysosomal membranes. Miyagi et al. J. Biol. Chem. 244: 5004–5011 (1999). A rat cytosolic sialidase DNA has also been reported. Miyagi et al., J. Biol. Chem. 244, 5004–5011 (1993). Interestingly, the latter genes have been sequenced and the bovine brain sialidase gene sequences do not share significant homology with previously reported bacterial, hamster, rat and human lysosomal and skeletal sialidase DNA sequences.

Treatment of cells with purified preparation of sialidase is known to affect a wide variety of cellular functions. It is thought that the wide variety of changes seen following such treatment is due to either the removal of terminal sialic acid residues from a glycoprotein or alternatively due to exposure of galactose residues. For example, treatment with purified sialidase disrupts receptor function, cell growth and differentiation, cell-cell binding and interactions, immunocyte function, and membrane fluidity, to name but a few Saito, M. and Yu, R. K., "Biochemistry and Function of Sialidases" supra.

SUMMARY OF THE INVENTION

It is therefore an object of the invention to provide an isolated single or double-stranded polynucleotide, typically DNA, having a nucleotide sequence which comprises a nucleotide sequence selected from the group consisting of: (a) the sense sequence of SEQ ID NO:1 from about nucleotide position 1 to about nucleotide position 1699; (b) polynucleotide sequences that, on expression, encode a polypeptide or polypeptides consisting of the amino acid sequences of SEQ ID NO:2; (c) polynucleotide sequences that encode amino acid sequences that are analogous to the amino acid sequence of SEQ ID NO:2, (d) polynucleotide sequences that are the polynucleotide complement of (a), (b) or (c), and (e) polynucleotide sequences that are substantially homologous to the polynucleotides of (a), (b) (c) and (d). It is further an object of the invention to provide contiguous polynucleotide fragments of the sequences in (a), (b), (c) or (d) of at least 16 nucleotides in length. In one particular embodiment, the polynucleotide is a DNA molecule, while in another embodiment the polynucleotide is an RNA molecule.

It is also an object of the invention to provide an expression cassette containing polynucleotide sequences that, on expression, encode a polypeptide or polypeptides consisting of the amino acid sequences of SEQ ID NO:2 (or analogous sequences), or fragments thereof, operably linked to at least one DNA control sequence.

It is also an object of the invention to provide a host cell transformed with polynucleotide sequences that, on expression, encode a polypeptide or polypeptides consisting of the amino acid sequences of SEQ ID NO:2 (or analogous sequences), or fragments thereof, operably linked to at least one control region and expressed in said host cell.

It is also an object of the invention to provide a method for producing large quantities of sialidase from a host cell transformed or transfected with mouse brain sialidase DNA.

It is also an object of the invention to provide a DNA probe that may be used to identify homologous sequences in other species.

The recombinant sialidase produced in accordance with the invention may be used for a variety of purposes including but not limited to enzyme replacement therapy for the therapeutic treatment of sialidosis and galactosialidosis. The isolated polynucleotide disclosed may further be used in gene therapy as a replacement for a mutated endogenous sialidase gene.

According to the invention, there is provided the polynucleotide sequence of SEQ ID NO:1 and the amino acid sequence of SEQ ID NO:2. The invention further provides the polynucleotide sequence of SEQ ID NO:1 or a polynucleotide encoding the amino acid sequence of SEQ ID NO:2, or portions thereof, operably linked to a control region and expressed in transformed or transfected cultured cells.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
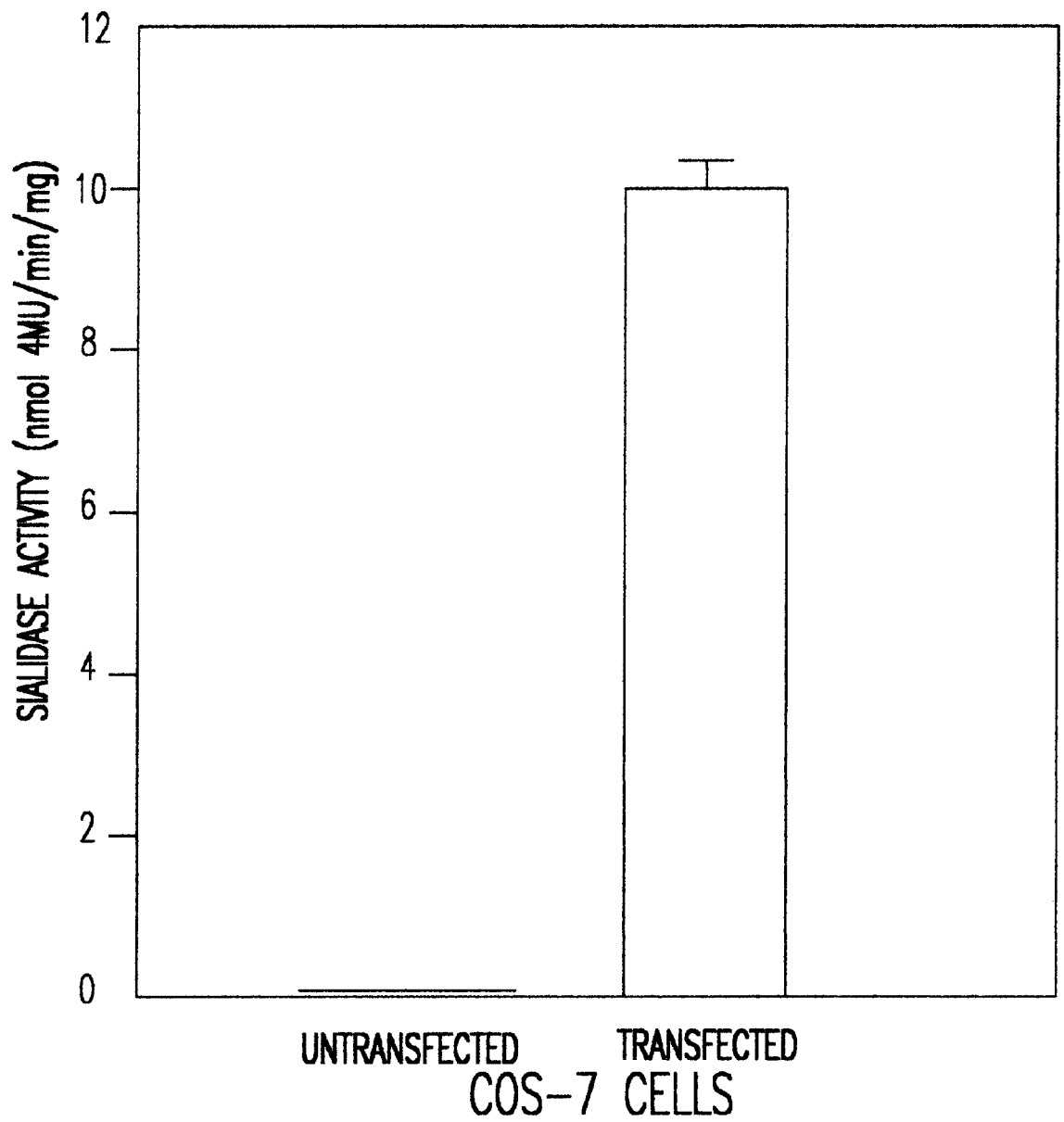
FIG. 1 is a graphical representation of the expression of the sialidase cDNA from mouse brain following transfection of COS-7 cells and transient expression of the sialidase cDNA cloned into the plasmid vector pCMV•SPORT2.

The Invention:

The present invention provides an isolated single or double-stranded polynucleotide encoding a sialidase gene from mouse brain cells. The invention also provides a heterologous host cell transformed with a polynucleotide encoding a sialidase gene from mouse brain cells. The invention further provides a general procedure for the in vivo production of mouse brain sialidase DNA in heterologous cells. The invention also provides a procedure for the in vivo production of mouse brain sialidase enzyme in heterologous cells lacking endogenous expression of mouse brain sialidase.

The invention further provides a method for expressing this gene in COS-7 cells. Expression of the sialidase gene can be achieved by placing the gene in an expression cassette and introducing the cassette into a suitable expression vector. In a particular embodiment of the invention, there is provided a transformed host containing a recombinant polynucleotide encoding all or part of the mouse brain sialidase gene operably linked to at least one regulatory sequence capable of directing the expression of the gene or portion thereof in eukaryotic cells. It can readily be seen by one skilled in the art, that the mouse brain sialidase gene can be transformed into a heterologous organism to accomplish expression of the gene by means of a transfer expression vector such as a plasmid. It can also be readily seen by one skilled in the art that the mouse brain sialidase gene operably linked to at least one regulatory sequence in the form of an expression cassette can stably be introduced into a host cell chromosome for stable transfection and expression of the sialidase gene.

The invention may be used to generate and/or construct polynucleotide probes which in turn may be used to identify sequences in other species that are substantially homologous to SEQ ID NO:1. Such polynucleotide probes can be comprised of radiolabels or other labels capable of detecting the presence of the labeled DNA. Such probes can be oligonucleotides or RNA or DNA fragments homologous to all or part of the mouse brain sialidase gene.

The invention may be used to detect at least one of the genes involved, either by its absence or by a characteristic mutation therein, in sialidosis in a subject (patient or fetus) affected or liable to be affected by this disease. The method comprising bringing a chromosomal DNA sample of this subject or fetus into contact with a DNA fragment homologous to the DNA of SEQ ID NO:1 or its complement, or a DNA primer homologous to a portion of SEQ ID NO:1 or its complement and detecting the absence or presence of specific DNA sequences within the sample. The skilled artisan can readily appreciate that DNA fragments or primers characteristic for SEQ ID NO:1 can be utilized to detect variations in the sialidase gene using DNA hybridization or Polymerase Chain Reaction (PCR) techniques, both of which are well known within the art. In the case of PCR analysis, primers that are homologous to a portion of SEQ ID NO:1 or its complement may designed by one skilled in the art such that a specific length PCR product can be generated based on the presence or absence of distinct sequences contained in SEQ ID NO:1. The subject DNA to be studied may be in the form of tissue biopsy samples or cells such as leukocytes, fibroblasts, and the like which can isolated from subjects by means well known within the art.

II. DEFINITIONS

A polynucleotide sequence can include, but is not limited to, prokaryotic DNA or RNA sequences, eukaryotic MnRNA, cDNA and synthetic DNA sequences, including those sequences that include any of the known base analogs of DNA and RNA residues.

A "double-stranded DNA molecule" refers to the polymeric form of deoxyribonucleotides (adenine, guanine, thymidine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed stand of DNA (i.e., the strand having a sequence homologous to the MRNA). A DNA sequence "corresponds" to an amino acid sequence if translation of the DNA sequence in accordance with the genetic code yields the amino acid sequence (i.e., the DNA sequence "encodes" the amino acid sequence).

Two DNA sequences are "substantially homologous" when at least about 85% (preferably at least about 90%, and most preferably at least about 95%) of the nucleotides match over the defined length of the DNA sequences.

Sequences that are substantially homologous can be identified in a Southern hybridization experiment under, for example, stringent conditions as defined for that particular system. Defining appropriate hybridization conditions is within the skill of the art. It is well known within the art that the parameters of hybridization, including the salt, temperature and time conditions may be varied and that the combination of parameters is more important than the measure of any single parameter. See, e.g., Wetmur and Davidson (1968) J. Mol. Biol. 31: 349–370. For a high degree of selectivity, relatively stringent conditions are used to form DNA duplexes, such as low salt (.02M to 0.15M NaCl) and/or high temperatures of between 50° C. and 70° C. For some applications, less stringent conditions such as 0.15M to 0.9M salt and 20° C.–50° C. temperatures will be optimal.

"Recombinant DNA" is a DNA molecule which includes DNA sequences obtained from two or more species.

A coding sequence is an in-frame sequence of codons that (in view of the genetic code) correspond to or encode a protein or peptide sequence. Two coding sequences correspond to each other if the sequences or their complementary sequences encode the same amino acid sequences. A "coding sequence" in association with appropriate regulatory sequences may be transcribed and translated into a polypeptide in vivo. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into MRNA which is then in turn translated into the protein encoded by the coding sequence.

For purposes of this invention, a cell has been "transfected" with or "transformed" by exogenous DNA when such exogenous DNA has been introduced inside the cell membrane. Exogenous DNA may or may not be integrated (covalently linked) to chromosomal DNA making up the genome of the cell. In procaryotes and yeast, for example, the exogenous DNA may be maintained on an episomal element such as a plasmid. With respect to eukaryotic cells, a stably transfected cell is one in which the exogenous DNA has become integrated into a chromosome so that it is inherited by daughter cells through chromosome replication. This stability is demonstrated by the ability of the eukaryotic cell to establish cell lines or clones comprised of a population of daughter cells containing the exogenous DNA. Cells that are "transiently" transfected are cells that will express the exogenous DNA for a limited time only, usually due to failure of the exogenous DNA to be stably integrated into the host chromosome.

"Vectors" are used to introduce a foreign substance, such as DNA, RNA or protein, into an organism. Typical vectors include recombinant viruses (for DNA) and liposomes (for protein). A "DNA vector" is a replicon, such as plasmid, phage or cosmid, to which another DNA segment may be attached so as to bring about the replication of the attached segment.

A "construct" is a vector which comprises a nucleic acid sequence of interest. For example, a construct may be a vector into which a nucleic acid sequence which encodes a polypeptide (such as a Sialidase polypeptide) has been cloned.

An "expression vector" is a DNA vector which contains regulatory sequences which will direct protein synthesis by an appropriate host cell. This usually means a promoter to bind RNA polymerase and initiate transcription of mRNA, as well as ribosome binding sites and initiation signals to direct translation of the MRNA into a polypeptide. Incorporation of a DNA sequence into an expression vector at the proper site and in correct reading frame, followed by transfection of an appropriate host cell by the vector, enables the production of a protein encoded by said DNA sequence.

A "DNA library" is a population of vectors which each contain a DNA coding sequence for some protein. The population as a whole encodes a large number of peptides, and the sequence for a particular one of the peptides can be recovered from the library using an appropriate screening procedure.

"Amplification" of nucleic acid sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8:291–294).

Two amino acid sequences are "substantially homologous" when at least about 90% of the amino acids match over the defined length of the amino acid sequences, preferably a match of at least about 92%, more preferably a match of at least about 95%.

An expression cassette comprises a promoter and/or other accessory control sequences discussed below that together are operational in a host cell and are operably linked to at least one coding sequence, whereby the efficient transcription and translation of the linked polynucleotide sequences contained therein confer a phenotype associated with the coding sequence in the host cell.

DNA "control sequences" refers to promoter sequences, ribosome binding sites, polyadenylation signals, transcription termination sequences, upstream regulatory sequences such as operators and repressor regions, enhancers, and the like, which collectively provide for the transcription and translation of a polynucleotide coding sequence or sequences in a host cell. Promoter sequences can include a constitutive promoter, an inducible promoter, or a series of promoters, as is well known in the art.

"Enhancer" sequences denote DNA regions that can cause an increase in expression of a gene when operably linked to the gene. The enhancer sequence can be operably linked in a wide variety of ways, both 5' and 3' to the gene, as is well known within the art.

"Operably linked" refers to an arrangement of elements wherein the components are configured so as to perform their usual function. Thus, control sequences operably linked to at least one coding sequence are capable of directing the expression of the coding sequence or sequences. The components may be separated by intervening DNA or contiguous, so long as the control sequence is capable of directing the efficient transcription and translation of the linked coding sequence or sequences.

A "coding sequence" or "sequence which encodes" refers to a polynucleotide sequence which is transcribed (in the case of DNA) and translated (in the case of RNA) into a polypeptide in vitro or in vivo when placed under the control of the appropriate control sequences. The boundaries of the coding sequence are determined by a translation start codon at the 5' amino end and a translation stop codon at the 3' carboxy terminus. A coding sequence can include but is not limited to, cDNA from prokaryotic or eukaryotic mRNA, genomic prokaryotic or eukaryotic DNA, and synthetic DNA sequences.

"Recovery" or "isolation" of a given fragment of DNA from a restriction digest means separation of the resulting DNA fragment on a polyacrylamide or an agarose cell by electrophoresis, identification of the fragment of interest by comparison of its mobility versus that of marker DNA fragments of known molecular weight, removal of the gel section containing the desired fragment, and separation of the gel from DNA. See, e.g., R. Lawn et al., 1981, Nucleic Acids Res., 9:6103, and D. Goeddel et al., 1980, Nucleic Acids Res., 8:4057.

"Transformation" means introducing DNA into an organism so that the DNA is replicable, either as an extra-chromosomal element or integrated into a chromosomal element. The methods used for transformation will vary depending upon whether the host cell is a eukaryote or a prokaryote. A preferred method for transformation of prokaryotes is the calcium chloride method as described in section 1.82 of Sambrook et al., in *Molecular Cloning A Laboratory Manual*, ($2^{nd}$ Ed. Cold Spring Harbor Laboratory Press 1989).

"Ligation" refers to the process of forming phosphodiester bonds between two double stranded DNA fragments using the enzyme ligase in a suitable buffer that also contains ATP.

"Oligonucleotide" refers to short length single or double stranded sequences of deoxyribonucleotides linked via phosphodiester bonds. The oligonucleotides may be chemically synthesized by known methods and purified on polyacrylamide gels.

III. Polynucleotides

The nucleotide sequence of the mouse brain sialidase gene is set forth in SEQ ID NO:1. The deduced amino acid residues of the mouse brain sialidase gene are set forth in SEQUENCE ID NO 2. Except where specifically noted, manipulations of DNA and bacterial and eukaryotic cells are performed as described by Sambrook et al., supra. As discussed below, the DNA sequence of the mouse brain sialidase bears some homology with viral, bacterial, and some human sialidase sequences but is substantially different and distinct form these sequences. At both the nucleotide and amino acid level. The sequences of the present invention share little or no homology with another brain (bovine) sialidase DNA that has been sequenced previously (Miyagi et al. 1999).

As is well-known in the relevant art, because of the degeneracy of the genetic code, there are many DNA and RNA molecules that can code for the same polypeptides as those encoded by the polynucleotides of the mouse brain sialidase gene described herein. A simple change in a codon may result in a changed polynucleotide that does not change the amino acid sequence or structure of the encoded polypeptide. Accordingly, substitutions of the codons recited in the present polynucleotide sequences with other equivalent codons can be made without departing from the scope of the present invention.

A table of amino acids and the representative abbreviations symbols and codons are set forth in Table II below:

TABLE I

| Amino Acid | Abbrev. | Symbol | Codons |
|---|---|---|---|
| Alanine | Ala | A | GCC, GCG, GCU |
| Cysteine | Cys | C | UGA, UGU |
| Aspartic Acid | Asp | D | GAC, GAU |
| Glutamic Acid | Glu | E | GAA, GAG |
| Phenylalanine | Phe | F | UUC, UUU |
| Glycine | Gly | G | GGA, GGC, GGG, GGU |
| Histidine | His | H | CAC, CAU |
| Isoleucine | Ile | I | AUA, AUC, AUU |
| Lysine | Lys | K | AAA, AAG |
| Leucine | Leu | L | UUA, UUG, CUA, CUC, CUG, CUU |
| Methionine | Met | M | AUG |
| Asparganine | Asn | N | AAC, AAU |
| Proline | Pro | P | CCA, CCC, CCG, CCU |
| Glutamine | Gln | Q | CAA, CAG |
| Arginine | Arg | R | AGA, AGG, CGA, CGC, CGG, CGU |
| Serine | Ser | S | AGC, AGU, UCA, UCC, UCG, UCU |
| Threonine | Thr | T | ACA, ACC, ACG, ACU |
| Valine | Val | V | GUA, GUC, GUG, GUU |
| Tryptophan | Trp | W | UGG |
| Tyrosine | Tyr | Y | UAC, UAU |

It is also well known in the relevant art that codons are also present in mRNA molecules and that such codons are characterized by the substitution of the base uracil in place of the base thymidine wherever thymidine is present in DNA. As noted, the present invention contemplates the mouse brain sialidase gene or portions thereof as an RNA molecule or molecules. Such RNA and DNA molecules that are complementary to the DNA sequences of the invention or portions thereof, or can hybridize under stringent conditions with these sequences, are also within the scope of the present invention.

The present invention also contemplates amino acid sequences that are analogous to the sequences set forth herein. Such analogous sequences are characterized by minimal changes in an amino acid residue or residues which do not alter the fundamental nature and biological activity of the mouse brain sialidase gene genes. It is well known in the relevant art that modifications and changes can be made in the structure of a polypeptide without substantially altering the biological function or activity of that polypeptide. In making such changes, substitutions of amino acid residues can be made on the basis of similarity of side chain substitutions. Such similarity can be in size, charge, hydrophobicity, hydrophilicity, and the like. As noted in U.S. Pat. No. 4,554,101, incorporated herein by reference, hydrophilicity values have been assigned to various amino acids. It is well known in the relevant art that an amino acid residue in some cases may be substituted for another amino acid residue having a similar hydrophilicity value without changing the biological activity of the analogous polypeptide.

Similarly, amino acid substitutions can be made on the basis of hydrophobicity, again often without changes in the biological activity of the analogous polypeptide from the original polypeptide.

As is also well known in the art, amino acid residues can be added to the amino acids of a known protein sequence without changing the biological activity of the known protein sequence. Furthermore, slight allelic variants of a protein sequence can be observed within a species that contain naturally occurring substitutions, deletions or additions of an amino acid residue or residues that do not alter or change the biological activity of the protein. Such naturally occurring amino acid variants are contemplated and considered within the scope of the present invention.

The expression constructs can be additionally modified according to methods known to those skilled in the art to enhance or optimize heterologous gene expression in plants and plant cells. Such modifications include but are not limited to mutating DNA regulatory elements to increase promoter strength or to alter the sialidase enzyme coding sequence itself. Also, in another embodiment, the sialidase gene may be linked to an inducible promoter so that the production of the sialidase enzyme is selectively initiated at a time in the host cell cycle whereby the yield of product is optimized. Such techniques are well known within the relevant art.

In order to provide quantities of a sialidase polypeptide sufficient for therapeutic or other use, appropriate coding sequences may be introduced into host cells which will express the polypeptide. Those of skill in the art will recognize that a plethora of possible expression systems exist and are well-known, as are the methods for introducing a vector which encodes the polypeptide, and various means for isolating and purifying a polypeptide of interest. Examples of suitable expression systems, include but are not limited to bacterial host cell systems (e.g. *Escherichia coli*), and eukaryotic systems (e.g. yeast, mammalian cells, and insect cells).

Expression constructs may be further modified according to methods known to those skilled in the art to add coding sequences that facilitate purification of the sialidase enzyme. In one non-limiting embodiment, a nucleotide sequence coding for the target epitope of a monoclonal antibody may be engineered into the expression construct in operative association with the regulatory elements and situated so that the expressed epitope is fused to the sialidase enzyme. For example, and not by way of limitation, a nucleotide sequence coding for the FLAG.TM. epitope tag (International Biotechnologies, Inc., IBI), which is a hydrophilic marker peptide, can be inserted by standard techniques into the expression construct at a point corresponding to the carboxyl-terminus of the sialidase enzyme. The expressed FLAG.TM. epitope-sialidase enzyme fusion product may then be detected and affinity-purified using anti-FLAG.TM. antibodies.

In another non-limiting embodiment, a nucleotide sequence can be engineered into the expression construct to provide for a cleavable linker sequence between the sialidase enzyme peptide sequence SEQ ID NO:2 and any targeting signal, reporter peptide, selectable marker, or detectable marker, that has not otherwise been cleaved from the sialidase enzyme peptide sequence SEQ ID NO:2 during peptide processing and trafficking through the host cell endomembrane system. Such a linker sequence can be selected so that it can be cleaved wither chemically or enzymatically during purification of the sialidase (Light et al., 1980, Anal. Biochem. 106:199–206).

In another embodiment of the invention, the sequences of SEQ ID NO:1 can be used as substrates for the generation of labeled DNA or RNA probes as is well known within the relevant art. These probes can be hybridized under stringent conditions with DNA from other species, such as humans, for example, to selectively identify and clone human sequences having substantial homology with the sequences disclosed herein.

In another preferred embodiment of the present invention, the detection of mutations and/or deletions in the sialidase gene may be at the genetic level. Examples include detecting the level of expression of mRNA which encodes the sialidase, or detecting a gene or segment of a gene which encodes a sialidase polypeptide, or detecting mutant forms of the gene. Any method of detecting the level of sialidase expression which is useful for the genetic profiling of mutations may be utilized in the practice of the methods of the present invention. The invention thus also contemplates the provision of oligonucleotide probes and primers which are complementary to and hybridize selectively with a portion of SEQ ID NO:1, and/or variations of SEQ ID NO:1 such as described above. In some preferred embodiments, such oligonucleotides may be at least about 10 consecutive nucleotides in length, or more preferably at least about 15 consecutive nucleotides in length, and most preferably at least about 20 consecutive nucleotides in length. Such oligonucleotides may be generated by any of a variety of methods which are well known to those of skill in the art, for example by using an automated DNA synthesizer. Such oligonucleotides may be used as probes as a part of a prognostic or diagnostic test kit for identifying cells or tissue which misexpress a sialidase protein, such as by measuring a level of sialidase encoding nucleic acid in a sample of cells from a subject e.g. detecting sialidase MRNA levels, or determining whether a genomic sialidase gene has been mutated or deleted. These oligonucleotides can be used to positionally locate mutations in a sialidase gene thereby predicting the phenotype of disease, such as the propensity to develop sialidosis. The means of utilizing such oligonucleotides as probes in this manner are well known to those of skill in the art.

Alternatively, in another preferred embodiment, sialidase may be introduced into cells via genetic means, (i.e. by "gene therapy" or "gene medicine", terms which are well known to those of skill in the art) for example by introducing a gene which encodes a Sialidase polypeptide, or by introducing an RNA molecule which encodes a sialidase polypeptide. Those of skill in the art will recognize that a variety of means exist for introducing nucleic acids into cells, including but not limited to the use of carrier molecules (e.g. vectors and lipids) as described below.

The sialidase nucleic acid molecules and sialidase enzyme of the invention can be incorporated into pharmaceutical compositions suitable for administration. Such compositions typically comprise the nucleic acid molecule or polypeptide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.TM. (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a sialidase enzyme or nucleic acid) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, including but not limited to retroviral or retroviral-based vectors and adenoviral and adenoviral-based vectors, the pharmaceutical preparation can include one or more cells which produce the gene delivery system.

The vector-containing composition is administered to a mammal in an amount sufficient to transfect a substantial portion of the target cells of the mammal. Administration may be by any suitable route, including oral, rectal, intranasal, or by intravesicular (e.g. bladder) instillation or injection where injection may be, for example, transdermal, subcutaneous, intramuscular or intravenous. Preferably, the expression vector is administered to the mammal so that the cells of the mammal are preferentially transfected. Determination of the amount to be administered will involve consideration of infectivity of the vector, transfection efficiency in vitro, immune response of the patient, etc. A typical initial dose for administration would be 10–1000 micrograms when administered intravenously, intramuscularly, subcutaneoulsy, intravesicularly, or in inhalation aerosol, 100 to 1000 micrograms by mouth, or $10^5$ to $10^{10}$ plaque forming units of a recombinant vector, although this amount may be adjusted by a clinician doing the administration as commonly occurs in the administration of other pharmacological agents. A single administration may usually be sufficient to produce a therapeutic effect, but multiple administrations may be necessary to assure continued response over a substantial period of time.

The pharmaceutical compositions can be included in a container, pack, or dispenser together with instructions for administration.

The present invention also provides a construct comprising a vector and a nucleotide sequence SEQ ID NO:1 which encodes a sialidase enzyme. The vector may also includes other elements, such as various control elements, sites for restrictions enzyme digestion, sequences which code for heterologous polypeptides, and the like. Such a construct may be useful as a template for the production of a sialidase polypeptide both in vitro and in vivo. The construct may be used in vivo, for example, as a carrier to deliver a sialidase encoding gene into cells.

The following detailed descriptions of the invention are provided to aid those skilled in the relevant art to practice the invention. Such detail is not, however, meant to limit the invention in any way. Modifications and variations on the detailed description in the preferred embodiments can readily be performed without departing from the spirit or scope of the claimed invention.

EXAMPLE I

Cloning of mouse brain sialidase.

Total RNA is isolated from mouse brains with the aid of Trizon reagent (Life Technologies) according to the manufacturers protocols. Reverse transcription of total RNA is performed in a reaction mixture containing oligo-dT primer and SuperScript II RNase H-Reverse Transcriptase (Life Technologies). Polymerase Chain Reaction (PCR) is then performed with Reverse Transcribed RNA as template using Platinum Taq DNA polymerase (Life Technologies) and the degenerate primers of SEQ ID NO 3: 5'-CTGCTNGCCTTTGCNGA-3' and SEQ ID NO:4: 5'-TCRTACAGRCACCCAAAYTG-3'. The following three-stage cycle is utilized for PCR: initial denaturation at 94° C. for 2 minutes; 35 cycles of denaturation for 30 seconds at 94° C., 30 seconds of annealing at 58° C., and a 1 minute extension at 72° C.; followed by a final 10 minute extension at 72° C. PCR products are then isolated following agarose gel electrophoresis using QIAquick Spin Purification products (Qiagen).

PCR fragments are then ligated with pGEM-T Easy Vector and colonies of E, coli JM109 cells are transformed with the ligation product are obtained for analysis of cloned fragments. Minipreps of plasmid DNA from isolated transformant colonies were sequenced using a BigDye Terminator Cycle Sequencing Kit (Perkin Elmer). Nucleotide sequences were compared to rodent cDNAs using Wisconsin Package Version 9.1 software (Genetics Computer Group0 A 796 base pair DNA product was obtained that is 84% identical to a cDNA sequence for rat skeletal muscle sialidase.

A mouse 15.5 day embryo "SUPERSCRIPT" cDNA library can be obtained from the manufacturer (Life Technologies catalog number 10667–012) and is amplified according to the manufacturer's protocol for semi solid amplification of plasmid cDNA libraries (Life Technologies). Pools of amplified primary cDNA transformants are prepared and screened using specific primers of SEQ ID NO:5 (5'-CCTCTTCCTTTTCTTCATCGCTGTCCC-3' and SEQ ID NO:6 (5'-TGGTTTAGGTACACACACCCAGGTTGGTTCTATTC-3'), which are derived from the 796 base pair fragment. The following three-stage cycle is utilized for PCR: initial denaturation at 94° C. for 2 minutes; 35 cycles of denaturation for 30 seconds at 94° C., 30 seconds of annealing at 68° C., and a 1 minute extension at 72° C.; followed by a final 10 minute extension at 72° C. Positive pools were plated onto Petri Dishes and screened by DNA probe hybridization using the amplified DNA fragment above as a labeled probe. Positive colonies are isolated, miniprep plasmid DNA is recovered, and the insert DNA sequenced using the BigDye Terminator Cycle Sequencing Kit as above.

Vectors for the expression of the present invention in eukaryotic cells ordinarily include (if necessary) DNA sequences for an origin of replication, a promoter located in front of the gene to be expressed, a ribosome binding site, an RNA splice site, a polyadenylation site, and a transcription terminator site. Alternatively, any or all of these sequences may be substituted by the analogous sequences of the sialidase gene. Promoters which may be used in the vectors to express the gene of the present invention are often of viral origin. These viral promoters are commonly derived from polyoma virus, adenovirus 2, Simian Virus 40 (SV40) and cytomegalovirus.

DNA sequences and the deduced protein sequences derived therefrom are determined using the Open Reading Frame Finder program (National Center for Biotechnology). Two potential open reading frames can be observed with this software: one showing a potential initiation codon at nucleotides 2–4 of SEQ ID NO:1, but it terminates in a stop codon at nucleotides 125–127 of SEQ ID NO:1. The second open reading frame is contained within nucleotides 176 of SEQ ID NO:1 to nucleotide 1294 of SEQ ID NO:1. This open reading frame is followed by a polyadenylation signal at nucleotides 1,658 to 1,663 and a polyadenylation signal at nucleotides 1677 to 1697. This open reading frame encodes a 41.6 kDa protein consisting of 372 deduced amino acid residues, with one potential N-glycosylation site located at Asn307. The Position-Specific Iterated Basic Local Alignment Search Tool (PSI-BLAST) program was used to search the GenBank peptide sequence database for sequences that are similar to the mouse brain sialidase. Other DNA and amino acid sequence analysis methods and software can readily be substituted for those mentioned herein and are contemplated by the present invention. The results of PSI-BLAST comparisons are shown in Table 1I.

TABLE 1I

| ORGANISM/SOURCE | IDENTITY[a] | SCORE[b] | EXPECT VALUE[c] |
| --- | --- | --- | --- |
| rat skeletal muscle | 84% (296/350) | 615 | $e^{-175}$ |
| Chinese hamster | 77% (272/350) | 573 | $e^{-163}$ |
| human lysosomal | 30% (72/237) | 55 | $6e^{-07}$ |
| mouse lysosomal | 28% (66/235) | 53 | $2e^{-06}$ |

[a]Identity represents the fraction and number of residues in the region of similarity which are identical.
[b]Score in bits represents similarity to mouse brain sialidase. A larger value indicates greater similarity.
[c]Expect Value describes the number of matches to a query sequence with a similar score due to chance in the GenBank peptide sequence database.

The sialidase amino acid sequence encoded within the DNA of the present invention exhibits some of the conserved sequences that are typically seen in sialidase enzymes. Examination of SEQ ID NO:2 reveals two amino acid sequence motifs conserved across the bacterial and eukaryotic sialidase sequences.

PHI-BLAST analysis also identified and aligned mouse brain sialidase to sialidases from the leech *Macrobdella decora*, and the bacteria *Salmonella typhimurium*, and *Micromonospora viridifaciens*. The two conserved sequence motifs are found in SEQ ID NO:2 that are characteristic for sialidase enzyme sequences: at position 26 to 32, wherein the F/YRIP conserved motifis located, and at positions 134 to 141 and 204–211, wherein the Asp box motif of the amino acid sequence "(amino)STDHGRTW (carboxy)" is observed.

EXAMPLE II

Transient transfection of COS-7 Cells with mouse brain sialidase.

COS-7 cells are grown on 60 mm tissue culture Petri dishes in serum-free DMEM (Dulbecco's modified Eagles medium) containing MEM-NEAA (minimum essential media-nonessential amino acids) solution until 80% confluent. Six micrograms per dish of the eukaryotic expression plasmid pCMV•SPORT2 containing SEQ ID NO:1 were used to transfect the COS-7 cells using Lipofectamine as described by the manufacturer (Life Technologies). Transfected cells and untransfected Cos-7 cell controls are harvested 72 hours after transfection by scraping the cells off of the petri dishes and suspending the cells in phosphate-buffered saline (PBS). The cell suspensions are then centrifuged at 10,000×g for 5 minutes at 4° C. and the supernate discarded. The cell pellets are resuspended in PBS and lysed by sonication on ice with a W-380 sonication (Heat Systems-Ultrasonics, Inc.). Protein concentration of cell lysates is then determined using the Bio-Rad Protein Assay system according to the manufacturer's directions (Bio-Rad Laboratories, Inc.).

The sialidase activity of cell lysates from cells transformed with the mouse brain cDNA insert were then determined by fluorimetric assay for the detection of umbelliferone that is released from 2'-(4-methylumbelliferyl)-a-D-N-acetylneuraminic acid in the presence of sialidase. Samples are incubated at 37° C. in a shaking water bath for 5 minutes. The reaction is then terminated and the fluorescence of the liberated umbelliferone is enhanced by the addition of 2 ml of 80 mM glycine-carbonate buffer, pH 9.7. Quantification of the product is made by measuring the fluorescence of the samples with excitation at 365 nm and emission at 450 nm using a standard of 4-methyl umbelliferone. Reactions were performed in triplicate using 250 mg cell homogenate in a final volume of250 ml containing 8 mM phosphate buffer (pH 7.4) and 2 mM 4-MUNeuAc. After incubation at 37° C. for 10 minutes, the reaction is terminated by adding 1 ml of 0.1 M 2-amino-2-methyl-1-propanol-HCl buffer (pH 10.3) on ice and centrifuged to remove insoluble material. Fluorescence is measured by a Shimadzu RF-5000 spectrofluorometer (Shimadzu Corp., Kyoto, Japan) with the excitation light at 365 nm and emission at 450 nm using 4-methylumbelliferone (4MU) as a standard.

The results of expression of the cDNA for mouse brain sialidase in COS-7 cells is shown in FIG. 1. The sialidase activity in COS-7 sells transfected with the cDNA of the present invention showed 10.78±0.78 nmol 4MU/min/mg protein. The untransfected controls exhibited 0.043±0.009 nmol 4MU/min/mg protein, indicating a 250-fold increase in sialidase activity following transfection and expression of SEQ ID NO:1 in COS-7 cells.

The mammalian host cells may be cultured in a variety of media. Commercially available media such as Ham's F10 (Sigma), Minimal Essential Medium, RPMI-1640 (Sigma), and Dulbecco's Modified Eagle's Medium may also be suitable for culturing the host cells. In addition, any of the media described in Ham and Wallace (Meth. Enz., 58:44 (1979) and Barnes and Sato (Anal. Biochem., 102:255, (1980) which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin), trace elements (defined as inorganic compounds usually present at final concentrations in the micromolar range), and glucose or an equivalent energy source. Any other necessary supplements may also be included at appropriate concentrations that would be known to those skilled in the art.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. An isolated single or double stranded polynucleotide which comprises the nucleotide sequence of SEQ ID NO: 1.

2. An isolated polynucleotide which is completely complementary to the polynucleotide of SEQ ID NO: 1.

3. A polynucleotide capable of selectively hybridizing to SEQ ID NO:1 or its complete complement under stringent conditions.

4. An expression cassette comprising an isolated single or double stranded polynucleotide encoding the amino acid sequence of SEQ ID NO: 2, wherein said polynucleotide sequence is operably linked to at least one regulatory sequence allowing the expression of the genes encoded on said expression cassette in a host cell.

5. Host cells transformed with an expression cassette comprising an isolated single or double stranded polynucleotide sequence encoding the amino acid sequence of SEQ ID NO: 2 wherein said polynucleotide sequence is operably linked to at least one regulatory sequence allowing the expression of the genes encoded on said expression cassette in the host cells.

6. The host cells of claim 5, wherein the cells are eukaryotic cells.

7. The host cells of claim 6, wherein the host cells are COS-7 cells.

8. The expression cassette of claim 4, wherein said regulatory sequence is an inducible promoter.

9. The expression cassette of claim 8 further comprising an enhancer sequence operably linked to said inducible promoter.

10. The host cell of claim 5, wherein the cell is a procaryotic cell.

11. A method for producing mouse brain sialidase which is enzymatically active, said method comprising:

a) culturing a host cell transformed or transfected with a recombinant expression construct comprising a nucleotide sequence encoding the protein of SEQ ID NO:2; and, b) recovering said sialidase.

* * * * *